United States Patent [19]

Shafer

[11] Patent Number: 4,678,894

[45] Date of Patent: Jul. 7, 1987

[54] SAMPLE IDENTIFICATION SYSTEM

[75] Inventor: John C. Shafer, Milford, Mass.

[73] Assignee: Baxter Travenol Laboratories, Inc., Deerfield, Ill.

[21] Appl. No.: 724,389

[22] Filed: Apr. 18, 1985

[51] Int. Cl.4 ............................................. G06F 15/20
[52] U.S. Cl. ..................................... 235/375; 235/462; 364/416; 435/808; 436/809
[58] Field of Search ....................... 235/375, 462, 493; 364/416, 478; 435/808; 436/809

[56] References Cited

U.S. PATENT DOCUMENTS

| | | | |
|---|---|---|---|
| 3,482,082 | 12/1969 | Israeli | 235/61.7 R |
| 3,565,582 | 2/1971 | Young | 23/230 |
| 3,656,473 | 4/1972 | Sodickson et al. | 128/2 R |
| 3,713,771 | 1/1973 | Taylor et al. | 23/230 R |
| 3,748,044 | 7/1973 | Liston | 356/180 |
| 3,754,444 | 8/1973 | Ure et al. | 73/423 A |
| 3,775,560 | 11/1973 | Ebeling et al. | 178/18 |
| 3,775,595 | 11/1973 | Rosse et al. | 235/61.6 H |
| 3,796,239 | 3/1974 | Zindler et al. | 141/83 |
| 3,831,006 | 8/1974 | Chaffin et al. | 235/61.7 R |
| 3,841,835 | 10/1974 | Kishimoto et al. | 23/253 R |
| 3,848,112 | 11/1974 | Weichselbaum et al. | 235/61.7 R |
| 3,916,157 | 10/1975 | Roulette et al. | 235/493 X |
| 4,116,775 | 9/1978 | Charles et al. | 435/808 X |
| 4,196,845 | 4/1980 | Chesters | 235/462 |
| 4,282,425 | 8/1981 | Chadima et al. | 235/462 |
| 4,358,203 | 11/1982 | Citrin | 356/432 |
| 4,363,782 | 12/1982 | Yamashita | 422/65 |
| 4,367,043 | 1/1983 | Sweet et al. | 356/338 |
| 4,394,567 | 7/1983 | Schoenhuber | 235/375 |
| 4,413,060 | 11/1983 | Assmann et al. | 436/47 |
| 4,460,824 | 7/1984 | Kadogaki | 235/375 |
| 4,471,218 | 9/1984 | Culp | 235/472 |
| 4,476,381 | 10/1984 | Rubin | 235/375 |
| 4,542,808 | 9/1985 | Lloyd et al. | 364/478 X |

Primary Examiner—David L. Trafton
Attorney, Agent, or Firm—Susan B. Fentress; Paul C. Flattery

[57] ABSTRACT

A system is described for keeping track of the identity of a plurality of individual medical samples when the samples are loaded into multiple holders in which each holder has multiple individual receiving locations. Each sample, holder, and receiving location of each holder has a unique identification number associated therewith. The system includes a recording means for displaying and storing signals. A first reader means is also provided for reading the unique holder identification numbers and generating a signal to be sent to the recording means for storage. A second reader means is also provided for reading the unique sample identification number for generating a second signal to be sent to the recording means for storage. A third reader means is also provided for reading the unique location identification number when the insertion device is introduced into a particular receiving location. The location signal is sent to the recording means for display purposes. A fourth reader means is also provided for reading the unique location identification when a sample is actually deposited in a particular receiving location to generate a signal to be sent to the recording means for storage. In a preferred embodiment, an error prevention means is provided to detect and possibly prevent various types of sample loading errors.

23 Claims, 13 Drawing Figures

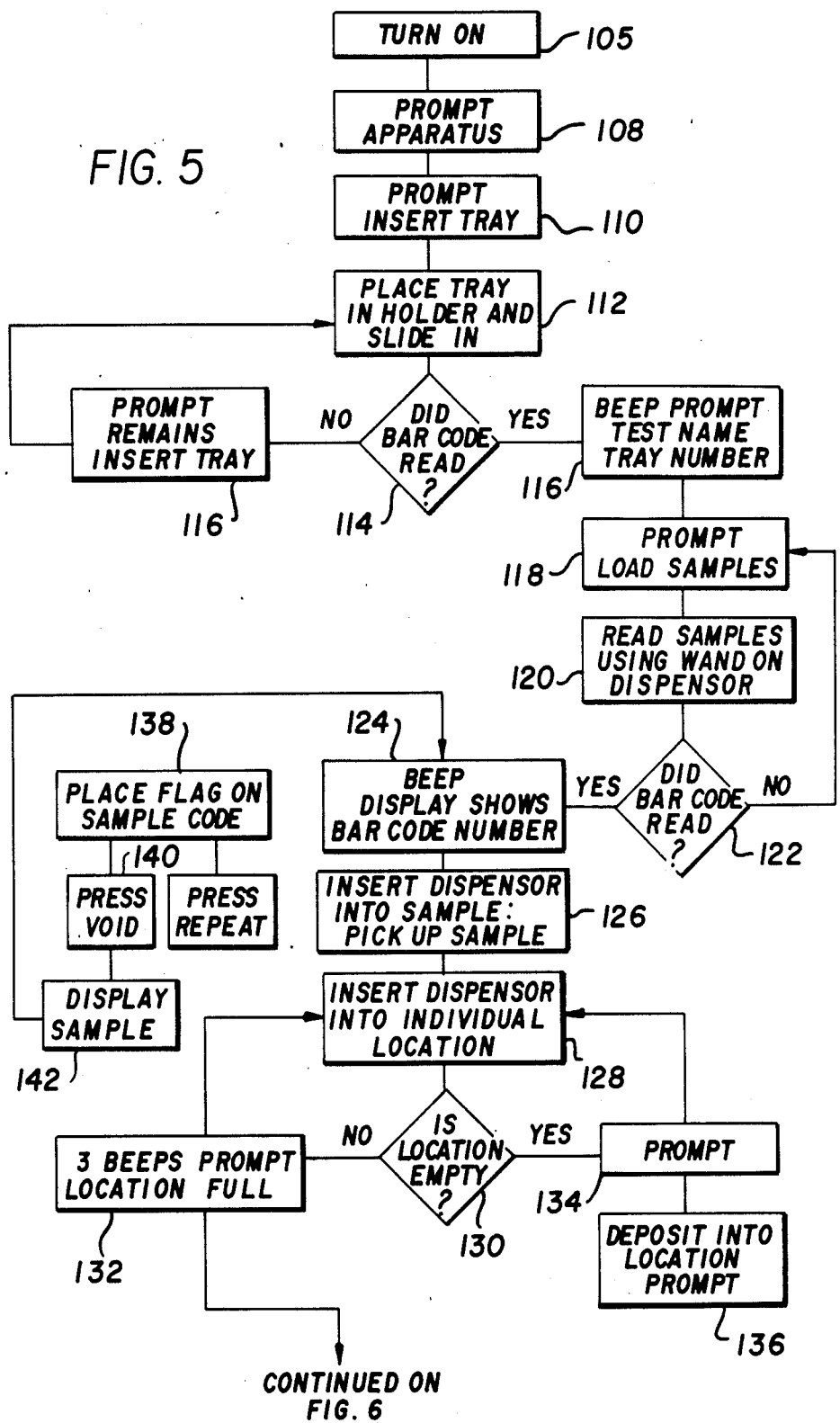

SAMPLE IDENTIFICATION SYSTEM

BACKGROUND OF THE INVENTION

This invention relates generally to systems for containing and identifying a plurality of samples and more specifically relates to medical analysis systems for identifying and analyzing multiple unique medical samples.

Those skilled in the art of medical-sample analysis are concerned with being able to identify the source from which a medical sample is taken throughout several procedures which are performed on the sample. These procedures may, or may not, require the sample to be transferred from one container to another. This concern by those skilled in the art is amplified when a vast number of samples are being simultaneously or sequentially analyzed. The need for maintaining the integrity of the identification of each sample is particularly acute when the results of the analysis have a potentially significant impact on a patient from which such a sample is taken. For example, if a patient sample is being analyzed to determine a method of treatment for a particular patient who is gravely ill, an error in identification of the sample during analysis may result in the death of the patient. In other instances, literally thousands of samples may be needed to be analyzed. In such instances, the need for a simple method of maintaining the integrity of the identification of each individual sample may be acute simply due to the vast number of unique samples being analyzed. An instance in which vast numbers of unique samples are to be analyzed exists in a blood bank environment. Typically blood banks are required to test each blood sample received to determine the presence or absence of hepatitis antigens. It is anticipated that in the future, blood banks will also be required to test each blood sample received for the presence or absence of an HTLV-III (Human T-Lymphotropic Virus, Type III) antibody which is known to be present when a patient has been exposed to the virus which is known to cause Acquired Immune Deficiency Syndrome, commonly known as AIDS.

In each of the preceding examples, it is highly desirable to be able to use a system which is very simple, from the operator's viewpoint, to transfer a blood sample or other material sample from one container to another without losing the identification of the source of the sample. Various systems have been developed in the past for transferring multiple samples and for identifying location positions. For example, U.S. Pat. No. 3,831,006 issued Aug. 20, 1974 to Chaffin, III et al., describes a patient-identification system. In this system, each patient receives a label representing a first unique random number. This number identifies the individual patient. When a blood, or other sample is taken from the patient, it is placed in a container that is labeled with a second unique random number. These numbers are machine readable and are fed into a computer for storage. If it is necessary to transfer the sample from the container into a subcontainer, the subcontainer is labeled with a third unique random number which is also fed into the computer. When an analysis is performed on the sample, the results of the analysis are also fed into the computer so that they may be correlated with the individual patient's identity. Such a system is useful in hospitals for collecting various samples from multiple patients for a variety of purposes.

Another system is described in U.S. Pat. No. 3,754,444, issued Aug. 28, 1973, to Ure at al. This system describes an automatic sampling and reading equipment and method for use in supplying biological samples to an automatic analyzer and in correlating test results from the automatic analyzer with the identity of the patient providing the sample. The equipment successively indexes, or moves, a tray of containers. Each container has a biological specimen therein. The equipment indexes the containers to a sampling station where a probe withdraws a sample of a desired amount of specimen. The equipment then indexes the container to a reading station where an encoded identification plate affixed adjacent to the container is electronically read. The samples are then delivered to an automatic analyzer which tests each sample. The output of the test results from the automatic analyzer, in the form of a strip chart, is correlated with a printout of the patient identification indicia sensed at the reading station so that the results of the test are properly related back to the correct patient from whom a specimen was originally taken.

Another system of interest is described in U.S. Pat. No. 3,775,560 issued Nov. 27, 1973 to Ebeling et al. This system is used to identify grid positions on a display device. In this system, a crossed light beam position encoder including x and y coordinate arrays of paired infrared light sources and detectors is described. These arrays cover a display device surface with x-and y-axis crossed light beams. A scanning means is coupled to the sources and detectors for electronically sequentially scanning the x-and-y axis rays so that only one source is emitting light and its associated detector is detecting light at any particular time. Means are included for noting the digital address of the beams during sequential scanning and for stopping the scan when the beams are interrupted. The digital address and, therefore, the position of the broken beams are transferred back to a computer.

While each of these systems described above has some usefulness in particular situations, it is desirable to be able to provide a system for handling multiple samples that is capable of detecting and possibly preventing various sample transfer errors which are likely to occur. For example, it is desirable to be able to provide a system which will warn against placing more than one sample in a single analyzer container. It is also desirable to be able to invalidate any test analysis results from a particular sample well if the well has been contaminated or otherwise invalidated due to a variety of causes.

SUMMARY OF THE INVENTION

The invention can be described as an apparatus for use with a plurality of materials. The apparatus includes a material-identification means for individually identifying each of the plurality of materials. The apparatus also includes a receiving means for receiving the plurality of individual materials. The receiving means includes a plurality of individual receiving locations and an array. Each receiving location is designed to receive an individual material sample. The apparatus also includes a location identification means for designating the unique location of each of the receiving locations. An insertion means is also provided for inserting an individual material into each of the individual receiving locations. The insertion means also includes a means for depositing the material into the individual receiving locations An insertion detection means is provided for detecting when insertion is occurring in an individual receiving location as identified by the location identification means. The apparatus of the subject invention also includes a recording means for recording the deposition of the individual material by the insertion means into the individual receiving locations. The recording means further includes a means for recording the location in which the individual material has been deposited as determined by the location-identification means and for recording the identity of the material as determined by the material-identification means.

Thus, an object of the invention is to provide a system for transferring a plurality of individual samples into individual sample containers in which the system is capable of determining whether an attempt is being made to transfer a second individual sample into a previously used sample container and for generating an alarm signal when such attempt occurs.

Another object of the invention is to provide a recording system which correlates unique sample-identification numbers with unique sample container locations and generates an invalid sample signal when two or more samples are deposited in a single sample container location.

Yet another object of the invention is to provide a system for electronically reading unique sample numbers, unique tray. container numbers, and unique sample location numbers as well as for electronically reading the particular analytical test to be performed on a series of samples.

And yet another object of the invention is to provide a system for recording, storing, and transferring electronic information representing medical samples, storage locations, and analysis information such that such information can be recorded and stored in a first recording apparatus, and then transferred to a second recording apparatus at a remote location.

Other objects, advantages, and novel features of the present invention will become apparent from the following detailed description of the invention when considered in conjunction with the accompanying drawings. Before explaining the emhodiments of the invention in detail, it is to be understood that the invention is not limited in its application to the details of the construction and to the arrangement of components as set forth in the following description, or as illustrated in the accompanying drawings. The invention is capable of other embodiments and of being practiced and carried out in various ways. Furthermore, it is to be understood that the phraseology and terminology employed are for the purpose of description and should not be regarded as limiting.

BRIEF DESCRIPTION OF THE DRAWINGS

FIG. 5 is a flowchart illustrating several aspects of the invention including detecting when a pipette dispenser has been inserted in the same receiving container in which another sample has been deposited and recording when a sample has been deposited in an individual receiving location;

DETAILED DESCRIPTION OF THE PREFERRED EMBODIMENT

Figure 1A:
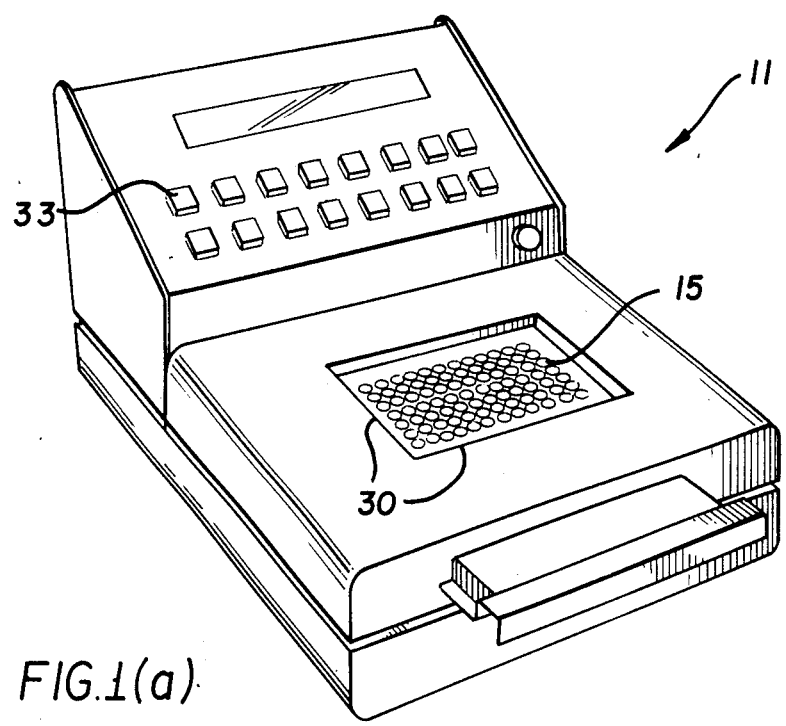
FIGS. 1(a) and (b) are perspective drawings illustrating the overall system of a preferred embodiment of the subject invention.
Figure 2A:
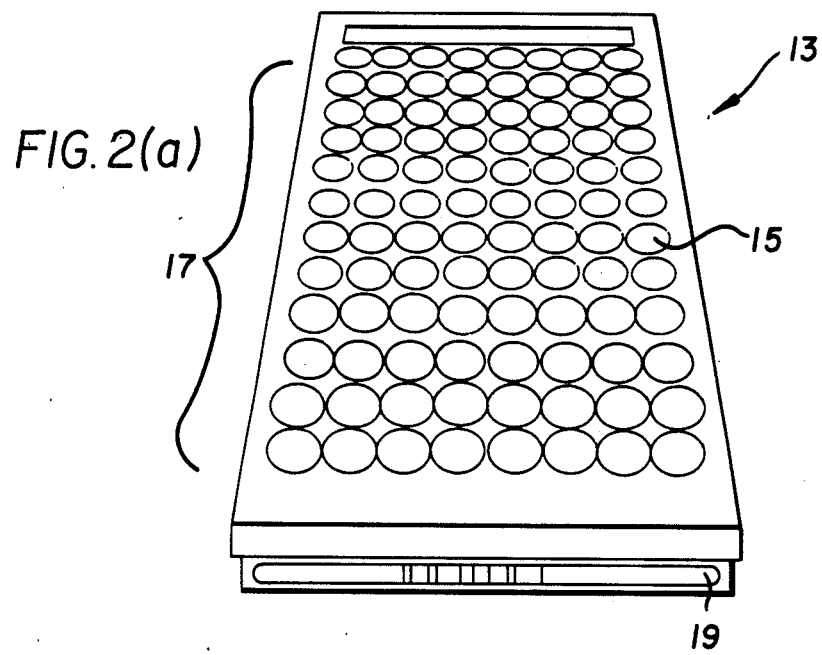
FIG. 2(a) is a perspective drawing of a microplate illustrating an array of individual receiving containers.

Refer now to FIG. 1(a), which illustrates a system 11 for identifying a plurality of individual medical samples which are to be analyzed. Typically, such a system would be used in a blood bank, laboratory, or other type of clinical-analysis laboratory for loading vast numbers of samples into a receiving means such as microwell tray 13, FIG. 2(a). The receiving means includes a plurality of individual receiving locations 15, or wells, in an array 17. Each well is used to receive an individual sample of material.

The microwell tray includes a tray identification receiving means 19 for receiving an insert 20 containing a bar code 21 which acts as a means for uniquely identifying each microwell tray. The bar code can also contain other types of information such as the particular type of analytical test to be run on a particular tray of samples. In the preferred embodiment, the inserts to identify each tray can be reused with succeeding batches or lots of analytical tests. This feature will be described in more detail below.

Figure 4A:
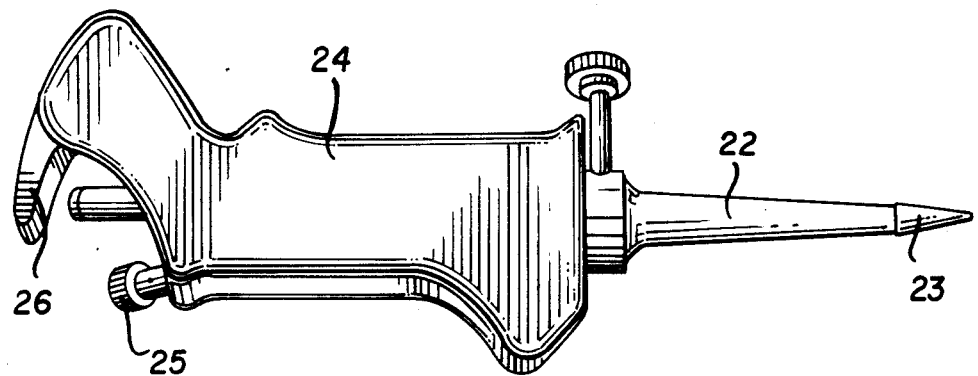
FIGS. 4(a) and (b) are perspective drawings illustrating a pipette dispenser used in one embodiment of the invention for inserting samples into individual containers and for releasing, or depositing, the samples into each container.

The subject invention includes an insertion means 22, FIG. 4A, for inserting individual samples or material into each of the receiving locations 15 of a microwell tray 13. In the preferred embodiment, a pipette tip 23 is attached to an electrically and mechanically operated withdrawing and dispensing gun 24. The gun 24 includes a trigger 26 which causes the gun to withdraw a sample from a test tube into pipette tip 23. The trigger 26 also causes any sample material which has been previously withdrawn into pipette tip 23 to be ejected. Thus, in a typical laboratory situation, an operator could insert pipette tip 23 into a test tube containing a material or sample to be analyzed and activate trigger 26. This would cause a portion of the sample to be withdrawn into the pipette tip. The operator would then insert the pipette tip of gun 24 into an individual receiving location 15 of the microwell tray 13. The operator could then activate the trigger 26 again to cause the gun 24 to operate as a means for depositing the individual material to be analyzed into a chosen individual receiving location or well of the microwell tray 13. The trigger 26 also generates a signal that is sent to a recording means when a sample is deposited in a tray to associate a particular sample identification number with a particular receiving location, and to record that the deposit has actually occurred. These features are discussed in greater detail below.

Figure 4B:
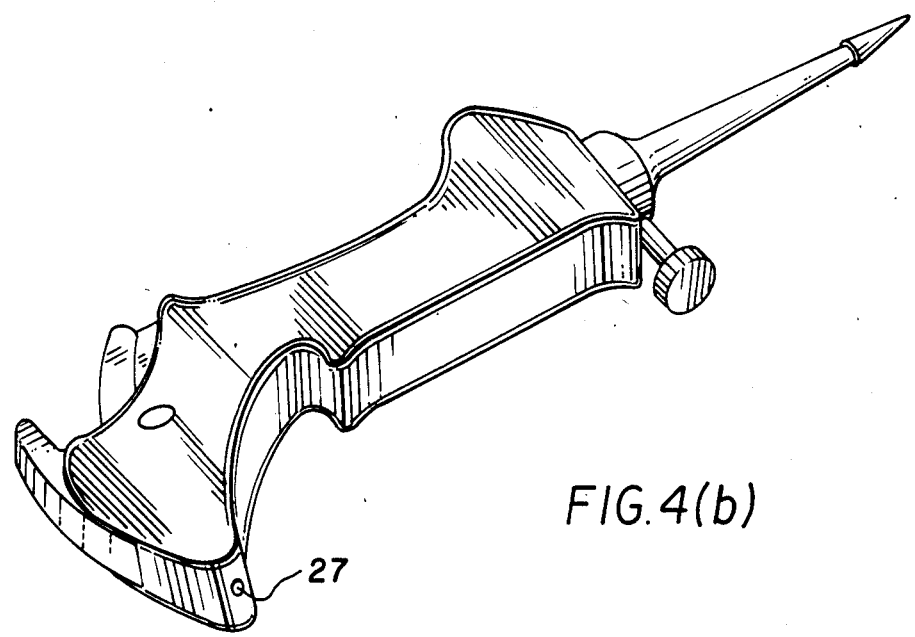

In the preferred embodiment, gun 24 also includes a barcode reader means 27, FIG. 4(b), to read bar codes which have been attached to each test tube containing a sample. In the preferred embodiment, each bar code on each test tube is a unique identification number. It is envisioned that in a typical laboratory using the preferred embodiment of the subject invention, the operator will use the bar code reader 27 to read the unique bar code attached to an individual sample test tube prior to withdrawing a portion of the sample into the pipette tip 23. Thus, the bar code reader 27 can act as a material identification means for individually identifying each of a plurality of individual samples to be analyzed.

Figure 1B:
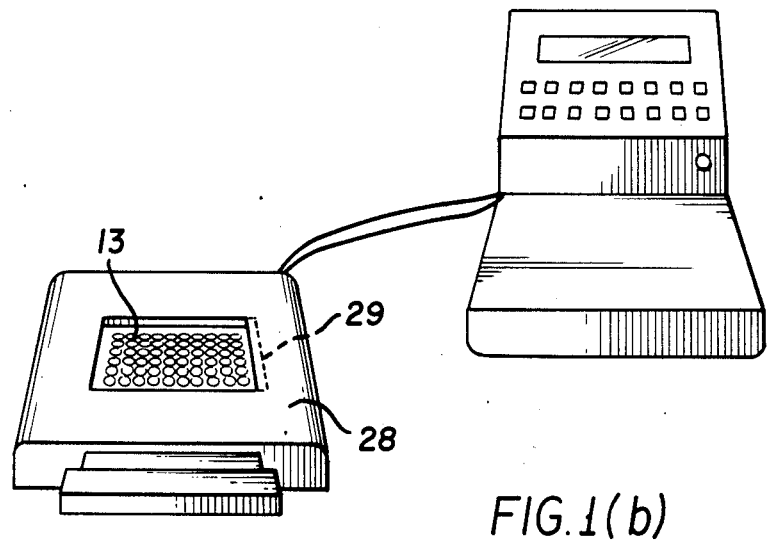

In the preferred embodiment, microwell tray 13 is inserted into a tray holder 28, FIG. 1(b). As the tray 13 is inserted into the tray holder 28, a bar code reader means 29, illustrated in phantom in FIG. 1(b), reads the bar code 21 located on insert 20 of the microwell tray 13. Thus, in the preferred embodiment, the bar code reader 29 can act as a reader means for reading a unique identification associated with each tray, or other type of holder, to generate a holder signal, which is sent to a recording means for storage. The recording means and its functions will be discussed in greater detail below.

In the preferred embodiment of the subject invention, a location-identification and reader means 30, FIG. 1(a), is provided. The location identification means is used to designate the unique location of each receiving location 15 in a microwell tray 13.

Figure 3:
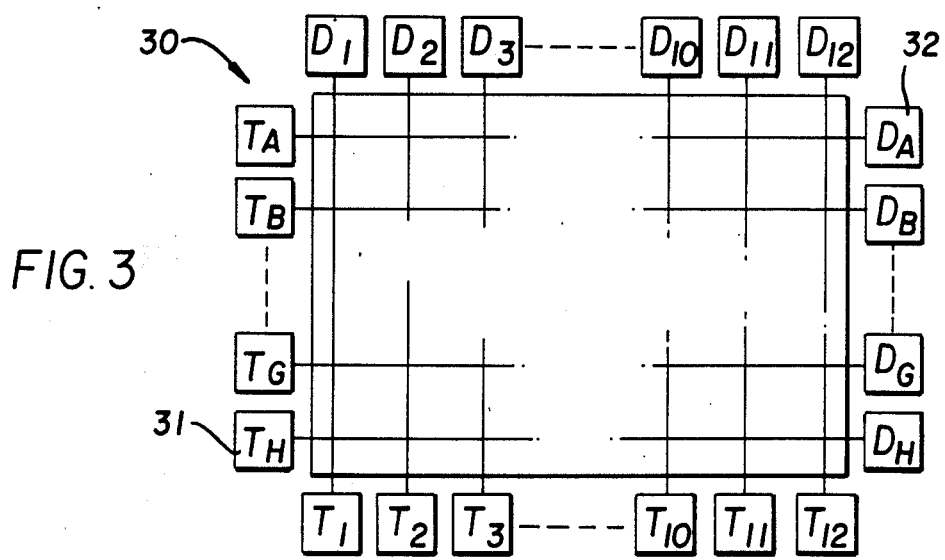
FIG. 3 is a schematic diagram of a photo array as can be used in one embodiment of the subject invention.

In one embodiment of the subject invention, the location- identification means may be a series of infrared light transmitters 31 and detectors 32 as illustrated in FIG. 3. Each transmitter 31 is coupled to a corresponding detector 32 to create a grid such that a light beam from a transmitter disposed along an x axis intersects with a transmitter along an y axis such that a single light beam intersection occurs above each individual well of the microwell tray. Thus, when the pipette tip 23 is inserted into a well 15, a corresponding pair of light beams which intersect above the well will be interrupted by the pipette tip. The interruption of light beams will be sensed by corresponding detectors which will generate a unique location signal identifying the particular well in which the pipette tip has been inserted. This signal is sent to a recording means discussed in greater detail for display in storage. In other embodiments, other reader means may be used to identify the particular location in which a sample has been stored. It should be noted that the infrared array can only detect when a pipette tip or other device has caused a pair of light beams intersecting above a well to be interrupted. The light array has no method of determining when a sample has actually been released from a pipette tip for deposition into a well in the currently preferred embodiment. In the preferred embodiment, trigger 26, FIG. 4(a) which acts to release a sample from the pipette tip into the well, also acts as a reader means to generate a signal which is used in conjunction with the signal generated by the light array reader means to be sent to the recorder means for recording when a particular sample has been deposited in a particular well location.

Referring again to FIG. 1(a), it should be noted that a manual entry means or keyboard 33 is available for manual entry of data. The operator may use the keyboard to perform several functions which will be discussed in greater detail below. Some of the functions that the operator can perform are manual entry of: (1) identification numbers; (2) tray identification numbers; (3) tests to be performed; and (4) any reagents that have been inserted. The keyboard can also be used to transmit data from the recording means and the system 11 to a remote recording means such as a mainframe computer of a separate clinical analysis device which will actually perform clinical tests on each of the samples.

Figure 2B:
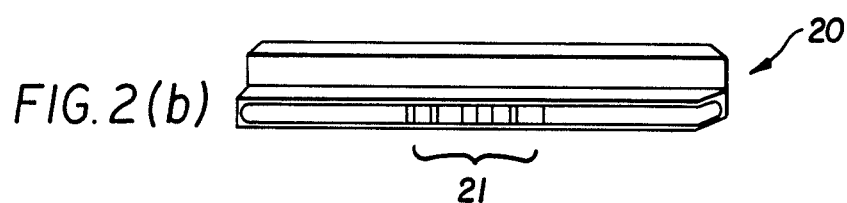
FIG. 2(b) is a perspective drawing of an identification insert for the microplate of FIG. 2(a)

Referring now to FIG. 5, the operation of the device used in the subject invention in the preferred embodiment will be described. After the apparatus is turned on, as illustrated by block 105 in FIG. 5, a prompt message 108 appears for approximately five seconds to identify the equipment for the user. After the identification message 108 has been displayed, a second prompt 110 is displayed. This prompt message 110 prompts the user to insert a tray into the device to cause a reader means to read a holder identification on the tray. In the preferred embodiment a microwell tray is used as illustrated in FIG. 2. After the user has placed the tray in a tray holder 112 and inserted the tray into the device, the device performs a check to determine if a bar code which has been placed on the side of the tray has been read as discussed above. If the bar code has not been properly read, a prompt 116 is displayed to tell the user to insert the tray into the device. If the bar code is properly read, the machine generates a beep prompt 116 in the preferred embodiment and identifies the test name to be performed and the unique tray number attached to the tray.

The machine then generates another prompt 118 to advise the user to load samples into the wells. The user then reads an individual sample bar-code number attached to the sample holder (not illustrated) using the pipette dispenser illustrated in FIG. 4 and also illustrated as block 120 in FIG. 5. The device then performs a check 122 to determine if the bar code on the sample was properly read. If the bar code was not properly read, in the preferred embodiment, the device remains in the prompt mode which informs the user to read the sample bar code again. If the bar code on the sample was properly read, the device generates a beep 124 and displays the bar code number from the sample on its display.

After the bar code on the sample has been properly entered into the device as illustrated by block 124, the operator then has several options for the next action to be taken. If the operator inserts the dispenser into a sample as illustrated by block 126 and inserts the dispenser into an individual receiving location as illustrated by block 128, the device then performs a check 130 to determine if the receiving location is empty. If the receiving location is not empty, the device generates three beeps and displays a prompt to inform the user that the particular location in which the pipette dispenser has been inserted is full. This is illustrated by block 132 in FIG. 5. On the other hand, if the check performed by the device indicates that the individual receiving location is empty, a prompt 134 will appear on the prompt screen to inform the user of the well number and of the sample number for the sample currently contained in the pipette dispenser as previously read by the bar code reader and illustrated by block 122. When the user sees prompt 134, this informs the user that the receiving location chosen is a valid receiving location and that the user may deposit a sample into the particular location chosen. If the user does deposit the sample into the well location chosen, as illustrated by block 136, the receiving location and associated sample number are then stored in the memory of the device. In the preferred embodiment, the memory is a nonvolatile memory so that if power to the device is interrupted, any information stored in the memory will not be lost.

As indicated previously, after the user has read the bar code on the sample container as illustrated by block 124, the user has several options with regard to the next action to be taken. Another option available to the user is to place a "flag" 138 on the bar code for an individual sample. This may be desirable if for some reason the sample will not be tested, yet it is desired to maintain a record of the individual sample. This may occur in several situations. For example in a blood collecting environment, if a blood donor is unable to donate a full unit of blood for some reason, it is desired to trace the unique bar code number associated with the partially full blood bag. This is desired in spite of the fact that the partially full bag will not be used and it is not necessary to perform any tests on the sample associated with that particular bag. This may be accomplished by generating a "void" entry 140 by the device. In the preferred embodiment, the user simply presses the "void entry button" on the keyboard as illustrated in FIG. 1. The display panel of the device then displays the sample number of the sample to be voided preceded by "V" as illustrated by block 142.

In some embodiments the void-sample number can be entered directly into the memory of the device immediately after the user has indicated that the sample number is to be a void-sample number. In the preferred embodiment, however, the subject invention is used for blood-sample analysis. In this context, the recognized practice is to actually insert a "pretend" sample into the pipette dispenser as illustrated by block 126, insert the dispenser into a desired receiving location 128, and actually deposit the void sample into the receiving location as illustrated by block 136. The act of depositing the void sample into a receiving location 136 causes the void sample number to be entered into the memory of the device in the preferred embodiment.

Figure 6:
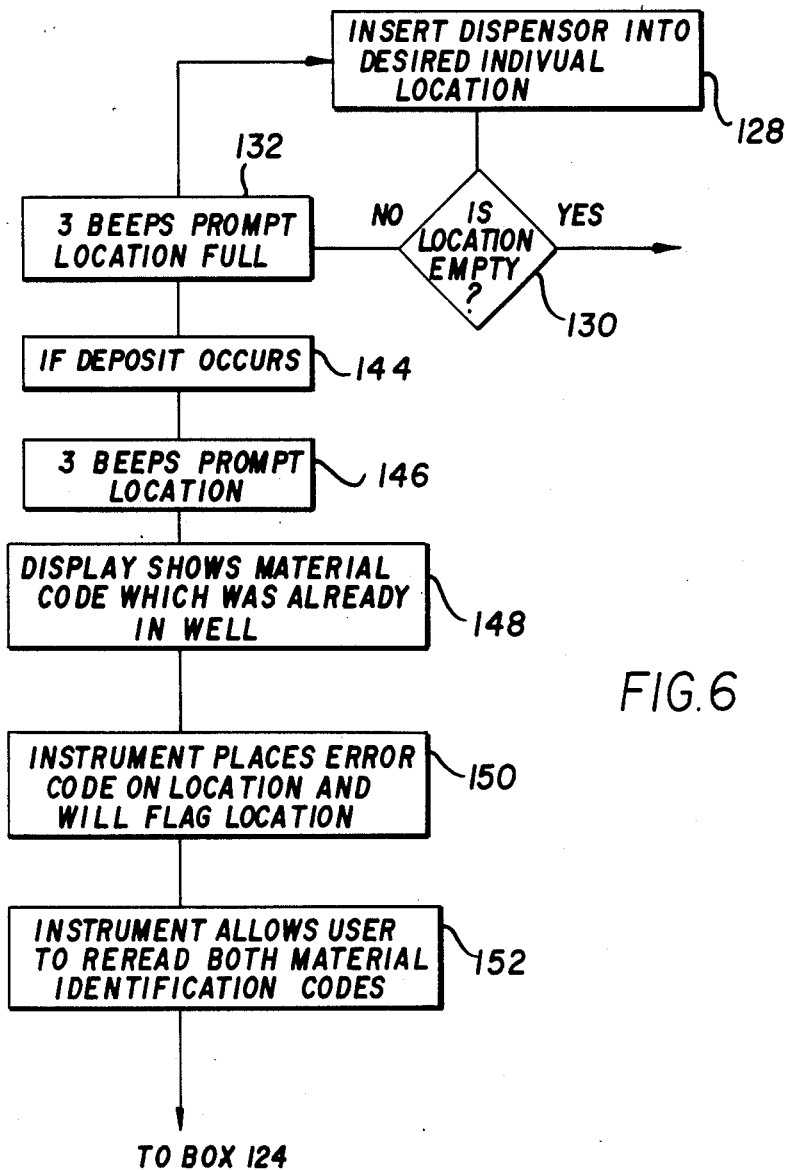
FIG. 6 is a continuation of the flow chart illustrated in FIG. 5 illustrating the generation of an error signal resulting from the deposition of more than one individual sample in a single receiving location.

Referring now to FIG. 6 which is a continuation of FIG. 5 beginning with block 128, another feature of the preferred embodiment of the subject invention is described. This feature relates to the instances in which two or more samples are deposited in a single receiving location. As discussed above, when a dispenser is inserted into an individual receiving location as illustrated by block 128, the device performs a check to determine if the location is empty as illustrated by block 130. If the receiving location is not empty, an audio warning is generated, three beeps in the preferred embodiment, as illustrated by block 132. This warns the user that the location has been previously used and is not available to receive an additional sample. If for some reason an additional deposit occurs in the sample well as illustrated by block 144, an additional audio prompt will occur consisting of three beeps in the preferred embodiment. The device also displays on the display screen an indication of the receiving location, an error designation, and the unique identification number for the sample that had been previously deposited in the same receiving location. This is illustrated by blocks 146 and 148. By creating a display of the sample number of the sample which had been previously deposited in the receiving location, the user is then able to locate the first sample that became invalidated when the second sample was deposited in the same receiving location. This is desirable because it allows the user to redeposit the first sample in another receiving location so that a valid test can be performed on the first sample.

In other embodiments of the subject invention, the display panel may alternately display the sample numbers of both samples that have been invalidated by the deposition of more than one sample in a single receiving location. Again, the purpose of alternately displaying invalidates sample numbers allows the user to redeposit each of the samples in different receiving locations so that valid tests can be performed on each sample. In the preferred embodiment, only the first invalidated sample number is displayed because it is assumed that the operator has the second invalidated sample in their hand when the error occurs which caused the second sample to become invalidated.

After the device displays the sample code for the first invalidated sample, as illustrated by block 148 in FIG. 6, the device records an error code for the particular receiving location which has been invalidated by the deposition of two or more samples in a single receiving location. This error code is recorded in the memory of the device. The sample code numbers for each of the invalidated samples are erased from the memory of the device as illustrated by block 152, FIG. 6. This allows the user to re-enter the invalidated sample numbers into new receiving locations as discussed in more detail below.

Figure 7:
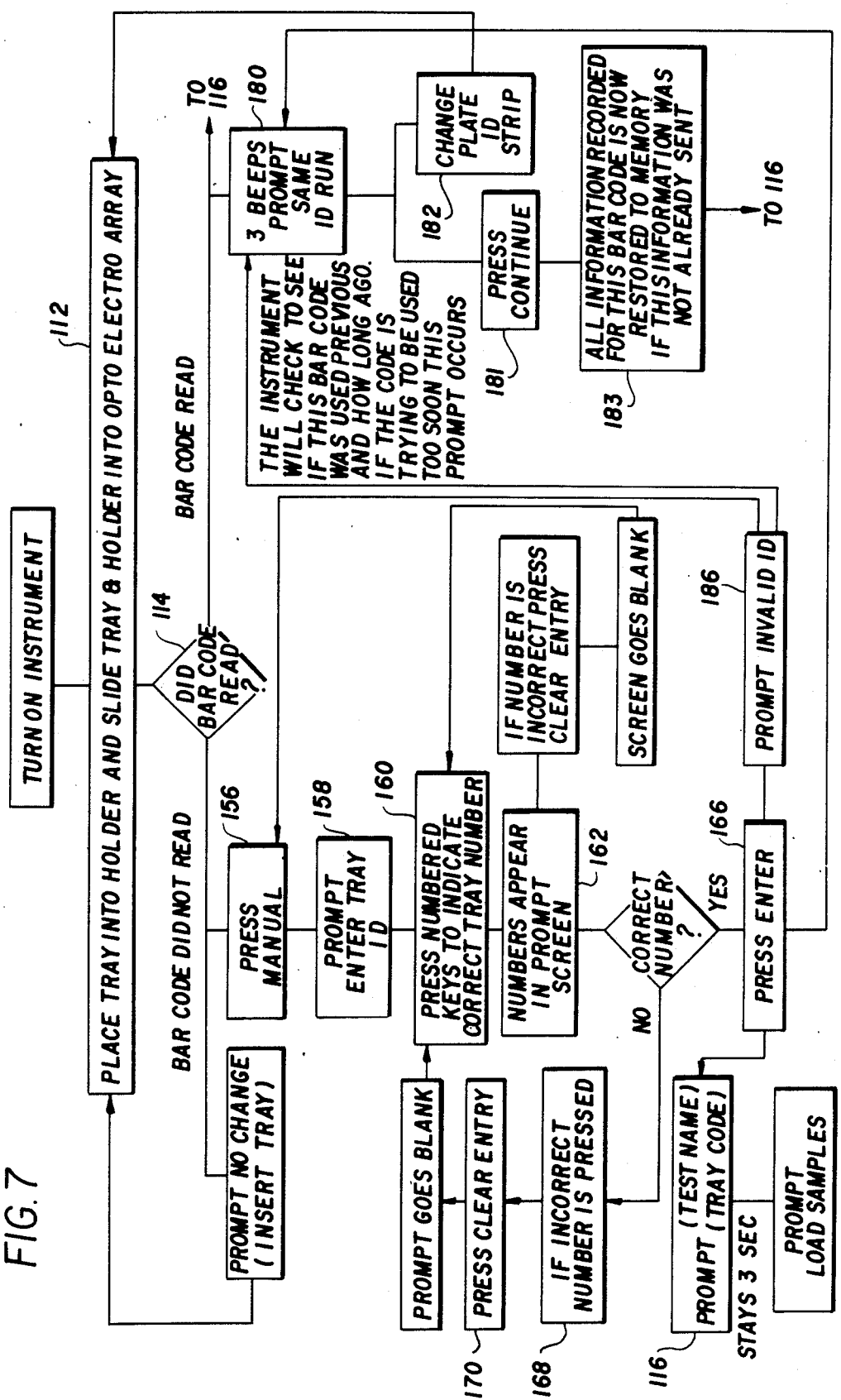
FIG. 7 is a continuation of the flowchart illustrated in FIG. 5 illustrating the ability of the user of the subject invention to manually enter tray identification numbers and the ability to reinsert a single tray into the preferred embodiment of the subject invention for subsequent loading of additional samples.

Refer now to FIG. 7 which illustrates several features of the invention including the ability to manually enter bar code numbers for microwell trays and also including various error generation capabilities of the device. After a microwell tray has been inserted into the device as illustrated by block 112, the device performs a check to read the bar code on the microwell tray as illustrated by block 114. This has been discussed in some detail above with respect to FIG. 5. If the bar code was not read properly, one option available to the operator in the preferred embodiment of the subject invention is to enter the bar code number manually. This is accomplished by striking the "manual" button on the keyboard illustrated in FIG. 1 on the outside of the device and as also illustrated by block 156 of FIG. 7. The device will then display a prompt requesting that the operator enter the unique identification number for the tray as illustrated by 158. The operator then enters the number manually using the number keys illustrated in FIG. 1 and also illustrated by block 160 in FIG. 7.

After the number has been manually entered, the tray identification numbers are displayed on the display screen as illustrated by block 162. The operator then checks to ensure that the entered number is the correct number. If the correct number has been entered, the operator presses the "enter" button on the device to cause the tray number to be stored in the memory of the device. This is illustrated by block 166. If an incorrect tray number has been manually entered by the user, as illustrated by block 168 in the preferred embodiment, the user simply clears the entry by pressing the clear entry. button illustrated in FIG. 1 and also illustrated by block 170 in FIG. 7. After the clear entry button has been pushed, the display screen goes blank and the user may re-enter the correct tray identification number and the process is repeated from block 160 of FIG. 7. After the correct number has been entered into the memory of the device, the device will either display a prompt informing the user of the tray code identification number, and any other associated information that is present on the bar code for the tray, or display an "invalid-tray code" identification prompt.

In the preferred embodiment, the bar code for the tray also contains information concerning the particular type of test to be performed on the samples that are placed in the tray. If an invalid tray code prompt appears, this means that the same tray code number has been previously stored in the memory of the device or that an incorrect test code incorporated in the bar code for the tray has been entered. This would occur in instances in which the same tray code had been previously inserted in the device. There are some situations in which it is desirable to reinsert the same tray code more than once into the device. This may occur if the tray is accidentally removed while samples are being loaded into individual microwells in the tray. In such instances, if the tray is not completely full, the user will typically desire to reinsert the tray to complete loading. In such instances, the user may press a "continue" button on the exterior of the device as illustrated in FIG. 1 to cause the device to accept the same tray number as previously received. The operator can then continue loading additional samples into unused individual receiving locations in the tray. The memory of the device will contain information from both times the tray has been inserted. This situation is illustrated by blocks 180–183.

In other instances, the operator may not wish to continue processing a tray having an identical bar code number as a previously entered tray. In these instances, the user must insert a different unique tray. identification number as illustrated by block 182. This will allow the operator to enter a new tray identification number by reinserting the tray with the new number.

In the preferred embodiment, the device is designed to allow duplicate tray numbers to be used only after twenty or more trays have been inserted into the device. This is to allow a laboratory to reuse the tray identification inserts 20 but not allow information to be associated with the tray I.D. number.

Figure 8:
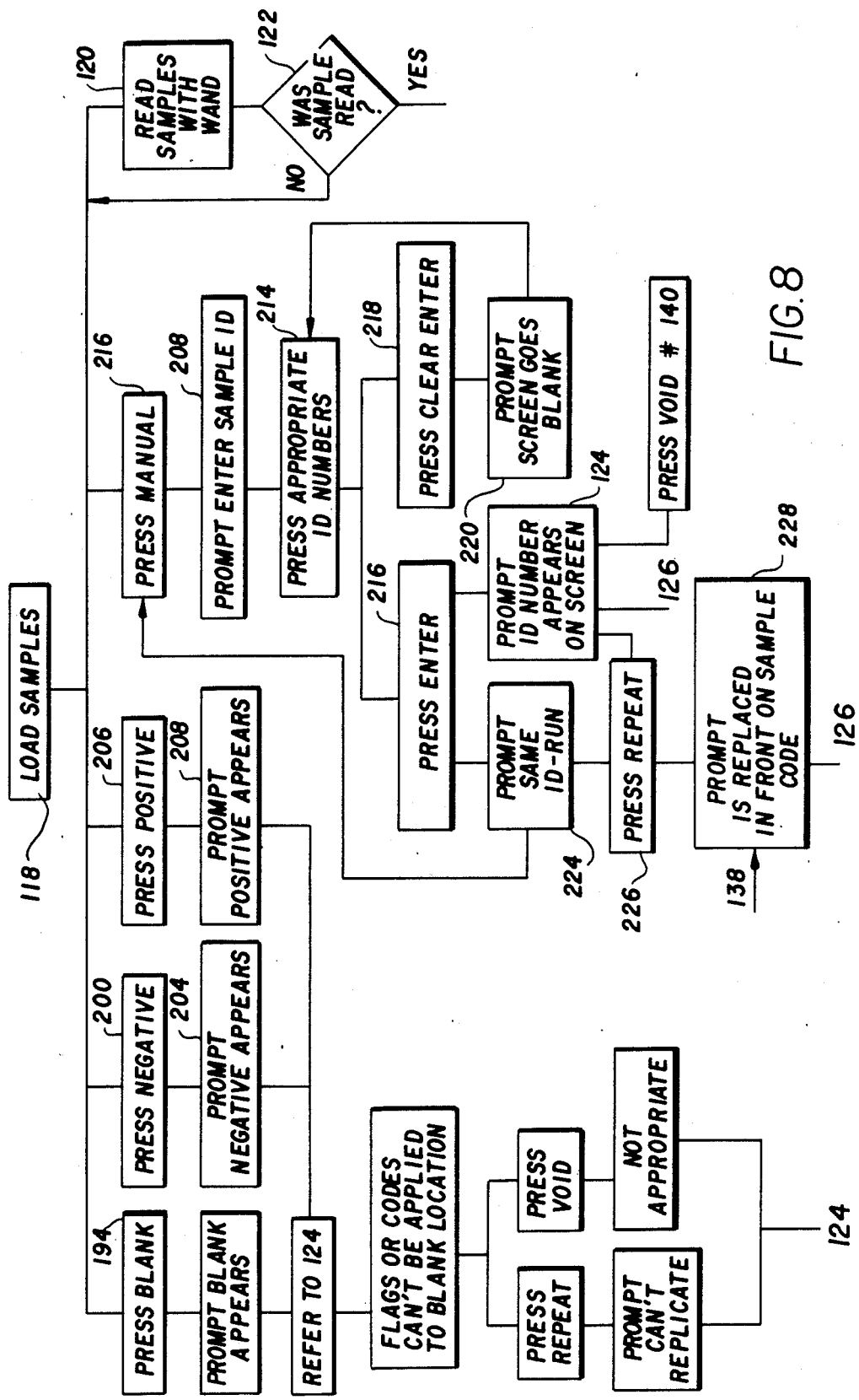
FIG. 8 is a continuation of the flowchart illustrated in FIG. 5 illustrating an expanded fashion, the options available to a user of the subject invention when loading samples into receiving locations.

Refer now to FIG. 8 which illustrates several features of the subject invention. These features involve the options available to the user of the device in loading samples into the receiving locations. This flowchart begins with block 118 of FIG. 5. In the preferred embodiment, when the device is ready to receive a sample identification number, a "load samples" prompt is illustrated on the display panel as illustrated by block 118 of FIG. 8. The operator then has five options available. The first option illustrated in FIG. 8 is to press the "blank" button on the exterior of the device as illustrated in FIG. 1 to allow the user to enter a blank sample into a receiving location. The act of striking the "blank" button is illustrated by block 194 in FIG. 8. The device responds by displaying a "blank" prompt on the display screen in place of a sample identification number as illustrated by block 124. A blank entry is used in situations in which the operator desires to purposefully leave an empty well in the tray. It should be noted that if a subsequent sample is then placed in a location which has been designated as a blank location, an error signal will result.

Another option available to the user when loading samples is to introduce a "negative" sample in a specific receiving location. A negative sample is a sample which is known to be lacking in a specific antigen, antibody or other entity that the other samples in the tray are being tested for. A negative sample is used for comparison purposes. To enter a negative sample in the preferred embodiment, the operator simply strikes the "negative" button on the keyboard of the device as illustrated in FIG. 1 and also illustrated by block 200 in FIG. 8. A prompt 204 then appears on the display screen indicating a negative sample identification designation in place of the usual unique sample identification number associated with an actual sample. The procedure for inserting the negative sample then continues in an identical manner that other actual samples are deposited into a receiving location to cause the device to store into its memory a particular receiving location associated with the negative sample.

Yet another option available to the user when loading samples is to introduce a "positive" sample into a specific receiving location. This is illustrated by block 206 in FIG. 8. Block 206 indicates that the user has pressed the "positive" button on the keyboard of the device as illustrated in FIG. 1. The positive sample is a sample that is known to contain the antigen or other entity for which the other samples are being tested. The positive sample, like the negative sample, is used for comparison purposes during analysis. When a positive sample is introduced, a "positive" prompt is displayed on the display screen as illustrated by block 208. In addition to loading positive or negative samples, the operator may use the insertion means to load reagents into individual receiving locations.

Yet another option available to the user when loading samples is to allow the user to manually enter sample identification numbers. This is illustrated by block 210. Block 210 indicates that the user has pressed the "manual" button on the exterior of the device as illustrated in FIG. 1. A prompt 212 will appear on the display screen to tell the user to enter a sample identification number. The user then enters the appropriate sample identification numbers as illustrated by block 214 using the number entry keys on the exterior of the device as illustrated in FIG. 1. After the user has entered the sample identification number manually, the user has two options. He may either strike the "enter" key illustrated by block 216 or, if the sample identification number has been incorrectly entered, the user may press the "clear" key illustrated by block 218.

If the enter key is used, one of two prompts will appear on the display panel. If the sample identification number is a new sample identification number that has not been previously used, the display panel will display the sample identification number as a prompt 220. On the other hand, if the same sample has been previously stored in the memory of the device, the device will display a prompt 224 indicating that the same identification number has been used previously. If the user wishes to enter the same sample more than once into the memory of the device during a single run, the user may press the "repeat" button on the keyboard of the device to allow the duplicate sample number to be accepted. This is illustrated by block 226. After the repeat button has been pressed, the display panel will display prompt 220 informing the user of the sample identification number and also display a prompt 138 which places a flag on the sample. In this instance the flag is to designate that a sample is being repeated. In the preferred embodiment, the flag is represented by an "R" 228 on the display panel.

The final option available to the user when loading sample identification numbers into the subject device is to read a sample identification number with a machine readable device as previously discussed with respect to block 120 in FIG. 5.

Figure 9:
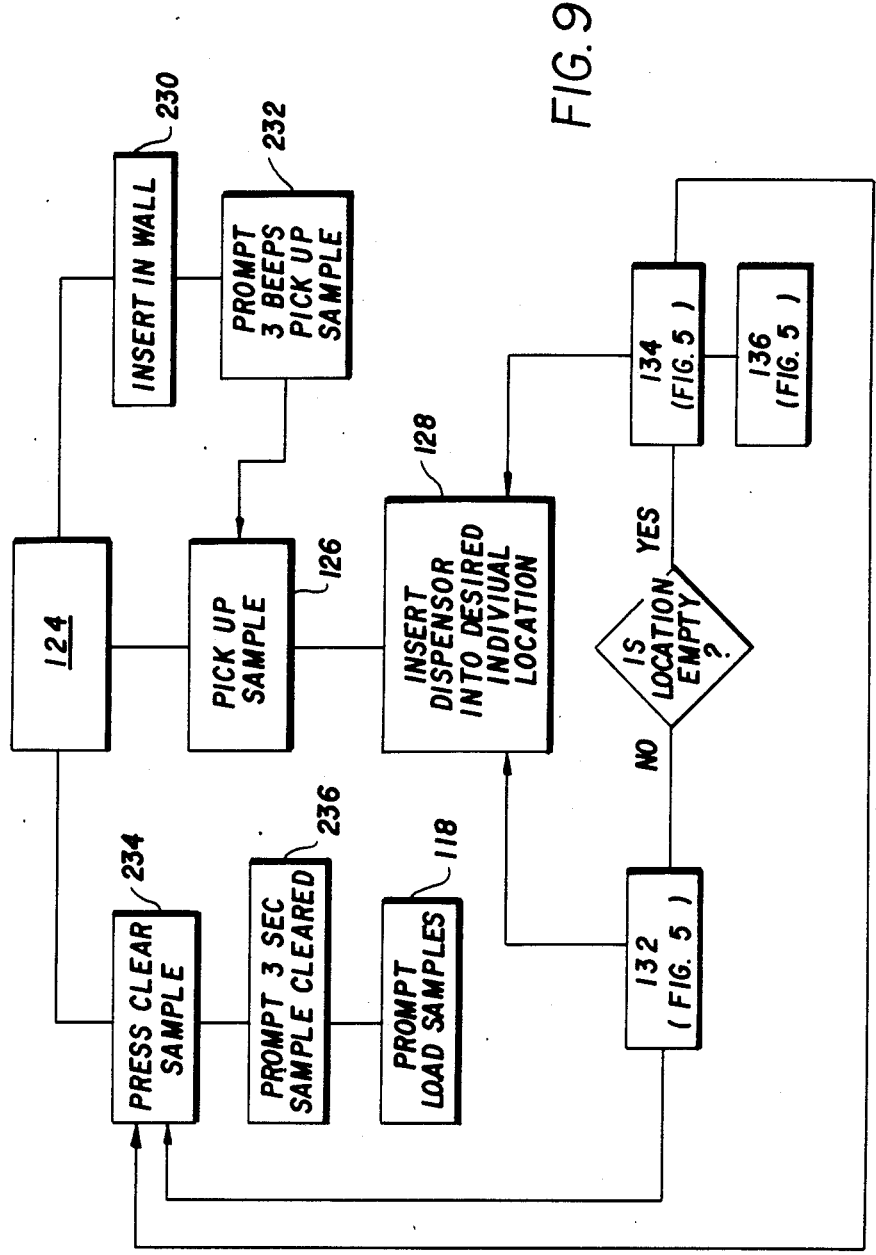
FIG. 9 is a more detailed flowchart of a portion of the flowchart in FIG. 5 illustrating the process involved in depositing a sample into a receiving location.

Refer now to FIG. 9 which describes in expanded detail several options available to the user in the preferred embodiment of the subject invention with respect to depositing a sample in a receiving location. FIG. 9 begins with block 124 of FIG. 5 of which is a prompt on the display screen of the device indicating a loaded sample identification number and any flags that have been associated with the sample. It should be remembered that the sample identification number is typically read by a bar code reader from a test tube containing the sample to be tested. In a typical operation, the user will first read the bar code from the test tube and then insert a pipette into the test tube to withdraw a portion of the sample. The sample is then deposited in a microwell in the preferred embodiment. FIG. 9 describes the typical operating situation as well as other situations which the preferred embodiment of the subject invention is capable of handling. After the display prompt indicating the sample identification number is displayed, as illustrated by block 124 in FIG. 9, the operator may insert a pipette into a well without first withdrawing a sample from the test tube. This is illustrated by block 230 in FIG. 9. This causes an error signal to occur which typically consists of three audio beeps and a visual prompt on the display panel to remind the user to withdraw a sample from the test tube. These prompts are illustrated by block 232. The operator may then pick up a sample as illustrated by block 126.

In other situations, it may be desirable for the user to clear a sample identification number prior to attempting to enter any samples into the tray. This is illustrated by block 234. The user simply presses the "clear" sample button on the exterior of the device. The device responds by displaying a "sample cleared" prompt on the display panel as illustrated by block 236. The sample cleared prompt typically lasts for three seconds in the preferred embodiment. After the sample-cleared prompt disappears, a "load samples" prompt returns to the screen as illustrated by block 118 in FIGS. 5 and 9.

Figure 10:
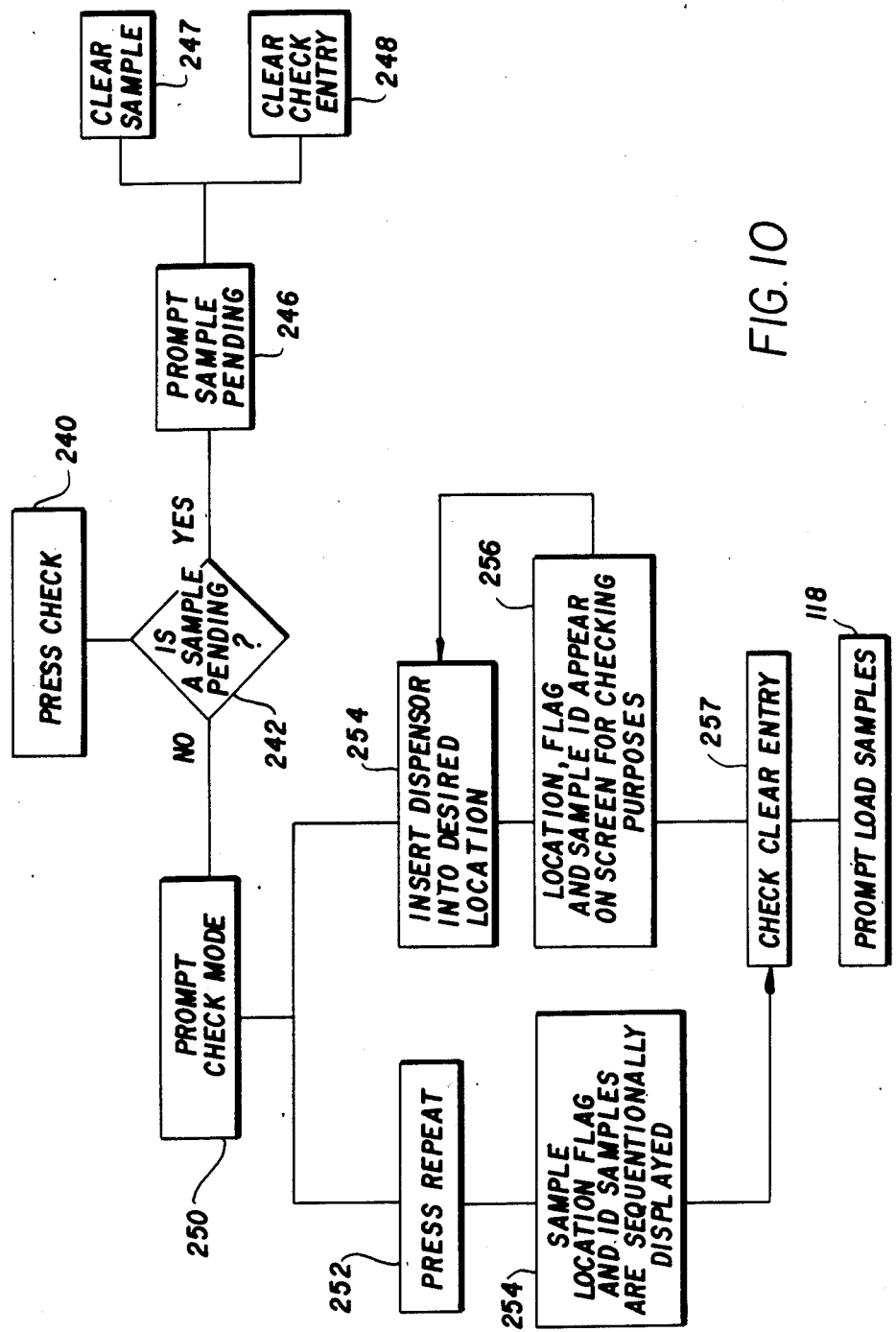
FIG. 10 is a flowchart illustrating several check procedures available to a user of the subject invention in the preferred embodiment.

Refer now to FIG. 10 which is a flowchart illustrating several "check" features of the preferred embodiment of the subject invention. At any time during the operation of the sample loading device after a tray has been inserted, the user may interrupt the loading procedure to perform a check on the status of the receiving locations in the tray. The check is initiated by the operator by striking the "check" button on the exterior of the device as illustrated in FIG. 1 and by block 240 in FIG. 10. When the check button is pushed, the device will perform a query 242 to determine if a sample is pending. If a sample identification number has been entered into the device, without associating the sample identification number with a receiving location, the device will refuse to perform further checks and will display a prompt 246 to indicate that a sample identification number is pending. The user may then either clear the sample identification number by striking the "clear" sample button as illustrated by block 247, or in the alternative, the user may cancel the check request by striking the "clear entry" button as illustrated by block 248.

If a sample is not pending, a prompt 250 will appear on the display screen to indicate that the device is in the "check mode". When the check mode prompt is displayed, the user has two options available. He may either press the "repeat" button as illustrated by block 252 or he may insert the sample dispenser in a particular location to be checked as illustrated by block 254. If the user does the latter, the display panel will display any information 256 that it has stored concerning that particular location. For instance, the display panel will display information relating to location, flags, and sample identification numbers associated with that particular location. This process can be repeated for any number of individual receiving locations.

As noted above, the user may strike the "repeat" button when the device is in the check mode. When the repeat button is used in the check mode, it causes the device to sequentially display all information associated with each individual receiving location. This is illustrated by block 254 in FIG. 10. After the user has received the desired information during the check procedure, the user may exit the check mode by simply pressing the clear entry button as illustrated by block 257. The device then returns to the mode illustrated by block 118 in FIG. 5 which is a prompt to load additional samples.

Although the invention has been described and illustrated in detail, it is to be clearly understood that the same is by way of illustration and example only, and is not to be taken by way of limitation; the spirit and scope of this invention being limited only by the terms of the appended claims.

That which is claimed:

1. Apparatus for use with a plurality of individual materials comprising:
   material-identification means for individually identifying each of said plurality of individual materials;
   receiving means for receiving said plurality of individual materials, said receiving means including a plurality of individual receiving locations in an array, each receiving location for receiving an individual material; location-identification means for identifying the unique location of each of said receiving locations within said array;
   insertion means for inserting an individual material from said plurality of individual materials into one of said individual receiving locations, said insertion means including a means for depositing said individual material into said individual receiving locations;
   insertion-detection means for detecting when insertion is occurring in an individual receiving location as identified by said location-identification means; and
   recording means for recording deposition of said individual material by said insertion means into said individual receiving locations, said recording means recording the identification of said unique location in which said individual material has been deposited as determined by said location identification means and for recording the individual identity of said material as determined by said material identification means.

2. Apparatus for use with a plurality of materials as recited in claim 1, further comprising:

error detection means for detecting any occurrence of an insertion of said insertion means in an individual receiving location in which said recording means has previously recorded the deposition of a material.

3. Apparatus for use with a plurality of materials as recited in claim 2, wherein:
said error detection means further includes warning means for generating an alarm signal when said insertion means is inserted into an individual receiving location in which said recording means has previously recorded the deposition of a material.

4. Apparatus for use with a plurality of materials as recited in claim 2, wherein:
said error-detection means further includes invalidating means for generating a first error signal when two individual materials have been deposited in a single individual receiving location, said invalidating means further including means for causing said recording means to record said first error signal designating that said individual receiving location in which two individual materials have been deposited contains invalid material.

5. Apparatus for use with a plurality of materials as recited in claim 3, wherein:
said error-detection means further includes invalidating means for generating a first error signal when two individual materials have been deposited in a single individual receiving location, said invalidating means further including means for causing said recording means to record said first error signal designating that said individual receiving location in which two individual materials have been deposited contains invalid material.

6. Apparatus for use with a plurality of materials as recited in claim 2, wherein:
said error-detection means further includes a detection-of-duplicate-material means for generating a second error signal when the same individual material as identified by said material-identification means is attempted to be deposited in more than one receiving location.

7. Apparatus for use with a plurality of materials as recited in claim 6, further comprising:
override means for cancelling said second error signal to allow an individual material to be deposited in more than one receiving location.

8. Apparatus for use with a plurality of materials as recited in claim 3, wherein:
said error-detection means further includes a detection-of-duplicate-material means for generating a second error signal when the same individual material as identified by said material-identification means is attempted to be deposited in more than one receiving location.

9. Apparatus for use with a plurality of materials as recited in claim 8, further comprising:
override means for cancelling said second error signal to allow an individual material to be deposited in more than one receiving location.

10. Apparatus for use with a plurality of materials as recited in claim 1, further comprising:
void-signal means for creating a signal for recordation by said recording means for identifying an individual identification from said material-identification means to trace an individual material that is not deposited in a receiving location.

11. Apparatus for use with a plurality of materials as recited in claim 1, wherein:
said material-identification means includes an optoelectrical device for sensing a pattern uniquely associated with each of said individual materials.

12. Apparatus for use with a plurality of materials as recited in claim 11, wherein:
said optoelectrical device is a bar-code reader.

13. Apparatus for use with a plurality of materials as recited in claim 1, wherein:
said material-identification means includes a keyboard for digitally entering a unique identification number associated with each of said individual materials.

14. Apparatus for use with a plurality of materials as recited in claim 1, further comprising:
second invalidating means for generating a second error signal for causing said recording means to record that a particular receiving location contains invalid material.

15. A system for identifying a plurality of individual medical samples, each sample having a unique sample identification associated therewith, said plurality of samples being contained in a plurality of holders, each holder having a unique holder identification associated therewith, each holder having a plurality of individual receiving locations, each receiving location having a unique location identification associated therewith, each receiving location for receiving a single individual sample from an insertion device, the system comprising:
recording means for displaying said storing signals;
first reader means for reading said unique holder identification associated with said holder and generating a holder signal to be sent to said recording means for storage;
second reader means for reading said unique sample identification associated with said medical samples and generating a sample signal to be sent to said recording means for storage; third reader means for reading said unique location identification associated with each individual receiving location when said insertion device is introduced into said receiving location and generating a first location signal to be sent to said recording means for display; and
fourth reader means for reading said unique location identification associated with each individual receiving location when a sample is deposited into said receiving location and generating a second location signal to be sent to said recording means, said location signal being associated with said sample signal generated by said second reader means.

16. A system as recited in claim 15, further comprising:
manual entry means for manually entering one of a holder identification, a sample identification, and a identification of a test to be performed as desired by an operator.

17. A system as recited in claim 15, further comprising:
display means for displaying to an operator a series of prompt messages to inform the operator to perform actions required to cause said first reader means to read said holder identification.

18. A system as recited in claim 17, further comprising:
first check means for determining if said holder identification read by said first reader means has been previously stored in said recording means, said check means including warning means for generating a first warning signal for the operator when said check means determines that said first reader means has read a holder identification that has been previously stored in said recording means.

19. A system as recited in claim 18, wherein said warning means further includes:
audio-means for generating an audio-detectable signal as said first warning signal, said display means also providing a visually detectable display as said first warning signal.

20. A system as recited in claim 17, wherein:
said display means includes a prompt to inform the operator when it is appropriate to load a sample into said insertion device.

21. A system as recited in claim 17, further comprising:
second check means for determining if a particular receiving location has previously had a sample deposited therein when said insertion means is inserted in said particular receiving location, said second check means including means for generating a second warning signal when said insertion means has been inserted in a receiving location that has had a sample previously stored therein.

22. A system as recited in claim 21, further comprising:
invalidation means for generating an invalidation signal associated with a particular receiving location for storage by said recording means when more than one sample has been deposited in said particular receiving location.

23. A system as recited in claim 15, further comprising:
flag means for flagging a sample identification signal for a particular sample to designate that said particular sample is one of a positive, negative, and void samples.

* * * * *

UNITED STATES PATENT AND TRADEMARK OFFICE
CERTIFICATE OF CORRECTION

PATENT NO. : 4,678,894
DATED : July 7, 1987
INVENTOR(S) : John C. Schafer

It is certified that error appears in the above-identified patent and that said Letters Patent are hereby corrected as shown below:

On cover sheet: correct spelling of Inventor's name from "John C. Shafer" to --John C. Schafer--

Signed and Sealed this

Second Day of August, 1988

Attest:

DONALD J. QUIGG

Attesting Officer

Commissioner of Patents and Trademarks